United States Patent
Kale et al.

(10) Patent No.: US 10,087,434 B2
(45) Date of Patent: *Oct. 2, 2018

(54) METHODS FOR EXTRACTING AND PURIFYING NON-DENATURED PROTEINS

(71) Applicant: Impossible Foods Inc., Redwood City, CA (US)

(72) Inventors: Aniket Kale, Foster City, CA (US); Ranjani Varadan, Fremont, CA (US); Simon Christopher Davis, San Francisco, CA (US)

(73) Assignee: Impossible Foods Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/661,873

(22) Filed: Jul. 27, 2017

(65) Prior Publication Data

US 2017/0321203 A1 Nov. 9, 2017

Related U.S. Application Data

(63) Continuation of application No. 15/515,938, filed as application No. PCT/US2015/053492 on Oct. 1, 2015.

(60) Provisional application No. 62/060,400, filed on Oct. 6, 2014, provisional application No. 62/058,211, filed on Oct. 1, 2014.

(51) Int. Cl.
*C12N 9/88* (2006.01)
*B01D 11/02* (2006.01)
*B01D 61/14* (2006.01)
*A23J 1/00* (2006.01)

(52) U.S. Cl.
CPC ............... *C12N 9/88* (2013.01); *A23J 1/006* (2013.01); *B01D 11/02* (2013.01); *B01D 61/145* (2013.01); *C12Y 401/01039* (2013.01)

(58) Field of Classification Search
None
See application file for complete search history.

(56) References Cited

U.S. PATENT DOCUMENTS

| | | | |
|---|---|---|---|
| 3,959,246 A | 5/1976 | Bickoff et al. | |
| 4,006,078 A | 2/1977 | Bickoff et al. | |
| 4,334,024 A * | 6/1982 | Johal | C12N 9/88 435/232 |
| 4,340,676 A | 7/1982 | Bourque | |
| 4,588,691 A | 5/1986 | Johal | |
| 5,151,358 A | 9/1992 | Heinsohn | |
| 5,328,841 A * | 7/1994 | Lorch | C11D 3/38645 435/209 |
| 5,407,810 A * | 4/1995 | Builder | C07K 1/1133 435/69.1 |
| 2004/0166026 A1 | 8/2004 | Bratcher et al. | |
| 2004/0171813 A1 | 9/2004 | Garger et al. | |
| 2006/0025579 A1 | 2/2006 | Riedl et al. | |
| 2010/0304126 A1* | 12/2010 | Wu | B27N 7/00 428/326 |
| 2012/0252065 A1* | 10/2012 | Rozenszain | A23J 1/14 435/68.1 |
| 2017/0321204 A1 | 11/2017 | Kale et al. | |

FOREIGN PATENT DOCUMENTS

| | | |
|---|---|---|
| WO | WO 2001/019969 | 3/2001 |
| WO | WO 2011/078671 | 6/2011 |
| WO | WO 2016/054375 | 4/2016 |

OTHER PUBLICATIONS

Gressent et al. Eur J Biochem. Jun. 2003;270(11):2429-35.*
Castro et al., Liquid-liquid equilibrium of water + PEG 8000 + magnesium sulfate or sodium sulfate aqueous two-phase systems at 35 oC: experimental determination and thermodynamic modeling, Braz. J. Chem. Eng., 22(3):463-470, 2005.
International Preliminary Report on Patentability in International Application No. PCT/US2015/053492, dated Apr. 4, 2017, 7 pages.
International Search Report and Written Opinion in International Application No. PCT/US2015/053492, dated Feb. 5, 2016, 10 pages.
Lamsal et al., "Separation of Protein Fraction in Alfalfa Juice: Effects of Some Pre-Treatment Methods," Trans. ASAE 46(3):715-720, 2003.
Yang et al., "Antihypertensive properties of spinach leaf protein digests," J. Agric. Food Chem. 52:2223-2225, 2004.
Degerli et al., "A novel concentration method for concentrating solutions of protein extracts based on dialysis techniques," Analytical Biochemistry, 297(2):192-194, Oct. 2001.
Srinivas et al., "Extraction and purification of a plant peroxidase by aqueous two-phase extraction coupled with gel filtration," Process Biochemistry, 35(1/2):43-48, Oct. 1999.
Supplementary European Search Report in European Patent Application No. 15846579.9, dated Feb. 5, 2018, 6 pages.

* cited by examiner

*Primary Examiner* — Christian L Fronda
(74) *Attorney, Agent, or Firm* — Fish & Richardson P.C.

(57) ABSTRACT

Materials and methods for extracting and purifying proteins are provided. For example, the materials and methods provided herein can be used for extracting and purifying proteins that denature at low temperature.

15 Claims, 11 Drawing Sheets

METHODS FOR EXTRACTING AND PURIFYING NON-DENATURED PROTEINS

CROSS-REFERENCE TO RELATED APPLICATIONS

This application is a continuation of U.S. application Ser. No. 15/515,938, filed Mar. 30, 2017, which is a National Stage application under 35 U.S.C. § 371 of International Application No. PCT/US2015/053492, having an International Filing Date of Oct. 1, 2015, which claims benefit of priority from U.S. Provisional Application Nos. 62/060,400, filed Oct. 6, 2014, and 62/058,211, filed Oct. 1, 2014, both of which are incorporated herein by reference in their entirety.

TECHNICAL FIELD

This document relates to materials and methods for extracting and purifying proteins, and particularly to materials and methods for extracting and purifying proteins that denature at low temperature.

BACKGROUND

Low temperature-denaturing proteins in their undenatured state are critical for the success of food replica products (e.g., cheese or meat replica products, such as beef replica products). Existing commercial protein extraction processes include unit operations and conditions that degrade the proteins, and are not useful in the manufacture of products containing such proteins. Further, most proteins have an associated color and odor, which can adversely affect their utility in food replica products.

SUMMARY

This document is based at least in part on the development of processes for extracting and purifying proteins from plant material, such that the proteins retain their non-denatured state without their associated colors and odors. For example, this document is based at least in part on the surprising discovery that hydrophilic polymers, and particularly polyethylene glycol (PEG), can adsorb color and odorous compounds from protein solutions.

In one aspect, this document features a method for purifying a protein from a biomass. The method can include extracting the biomass with an aqueous solution containing PEG and, optionally, a flocculant, to generate an extraction slurry that contains bulk solids and an extract; optionally adjusting the pH of the extraction slurry to a pH of 2 to 10; collecting the extract and adding salt to form a two-phase mixture; separating the two-phase mixture to generate a PEG phase and a product phase; and collecting and filtering the product phase to generate a filtered product phase that contains the protein. The biomass can include plant material. (e.g., flowers or leaves). The plant can be alga, maize, wheat, rice, sorghum, rye, canola, millet, barley, soybean, sunflower, safflower, tobacco, alfalfa, potato, *Brassica* spp., cotton, tomato, or tobacco. The protein can be rubisco. The PEG can have a molecular weight of about 8000. The flocculant can include alkylamine epichlorohydrin. The salt can include magnesium sulfate. The separating step can include gravity settling or centrifugation (e.g., using a disk stack centrifuge). The filtering can include microfiltering. The method can further include concentrating and diafiltering the filtered product phase to generate a product concentrate. The diafiltering can include using an ultrafiltration membrane system. The method can further include sterilizing the product concentrate to obtain a sterilized product concentrate. The sterilizing can include UV irradiation, pasteurization, or microfiltration. The method can further include drying the sterilized product concentrate. The drying can include using a spray dryer or a freeze dryer under mild conditions.

In another aspect, this document features a method for removing impurities from a protein solution. The method can include adding a hydrophilic polymer and a salt to the protein solution to generate a polymer rich phase and a protein phase, and separating the polymer rich phase from the protein phase. The hydrophilic polymer can be PEG. The PEG can have a molecular weight of about 8000. The method can further include adding a flocculant to the protein solution. The flocculant can contain alkylamine epichlorohydrin. The salt can include magnesium sulfate. The method can further include adjusting the pH of the protein solution to a pH of 2 to 10. The protein can be rubisco. The separating can include gravity settling or centrifugation (e.g., centrifugation using a disk stack centrifuge). The method can further include filtering the protein phase to generate a filtered product phase (e.g., by microfiltering). The method can further include concentrating and diafiltering the filtered product phase to generate a product concentrate. The diafiltering can include using an ultrafiltration membrane system. The method can further include sterilizing the product concentrate to obtain a sterilized product concentrate (e.g., by UV irradiation, pasteurization, or microfiltration). The method can further include drying the sterilized product concentrate (e.g., using a spray dryer or a freeze dryer under mild conditions).

This document also features a composition containing rubisco and a hydrophilic polymer, wherein the hydrophilic polymer is present at a concentration of less than about 0.1% (w/w). The hydrophilic polymer can be PEG. The hydrophilic polymer can be present at a concentration less than about 0.01% (w/w).

In another aspect, this document features a method for purifying a protein, where the method includes providing a protein suspension from which solids have been removed; optionally adding salt to the protein suspension; optionally adjusting the pH of the protein suspension to a pH of 2 to 10; dialyzing the protein suspension against a PEG solution, or subjection the protein suspension to ultrafiltration with PEG on the permeate side of the membrane; and subjecting the dialyzed or ultrafiltered protein solution to one or more concentrating or filtering steps to generate a product phase that contains the protein. The protein suspension can contain one or more proteins from plant material. The plant material can include flowers or leaves. The plant can be alga, maize, wheat, rice, sorghum, rye, canola, millet, barley, soybean, sunflower, safflower, tobacco, alfalfa, potato, *Brassica* spp., cotton, tomato, or tobacco. The protein can be rubisco. The PEG can have a molecular weight of about 8000. The providing step can include extracting a disintegrated biomass to remove the solids and generate the protein suspension, optionally with addition of a flocculant to the biomass. The flocculant can include alkylamine epichlorohydrin. The extracting can include using gravity settling or centrifugation to separate solids from the protein suspension. The salt can include magnesium sulfate. The one or more filtering steps can include diafiltering. The method can include concentrating and filtering the dialyzed or ultrafiltered protein solution to generate a product concentrate. The method can further include sterilizing the product concentrate to obtain a sterilized product concentrate, and/or drying the sterilized product concentrate (e.g., using a spray dryer or a freeze dryer under mild conditions).

In still another aspect, this document features a method for purifying a protein, comprising providing a protein suspension from which solids have been removed; optionally adding salt to the protein suspension; optionally adjusting the pH of the protein suspension to a pH of 2 to 10; applying the protein suspension to a support comprising PEG; and collecting the protein phase that is not retained on the support. The protein suspension can contain one or more proteins from plant material. The plant material can include flowers or leaves. The plant can be alga, maize, wheat, rice, sorghum, rye, canola, millet, barley, soybean, sunflower, safflower, tobacco, alfalfa, potato, *Brassica* spp., cotton, tomato, or tobacco. The protein can be rubisco. The PEG can have a molecular weight of about 8000. The providing step can include extracting a disintegrated biomass to remove the solids and generate the protein suspension, optionally with addition of a flocculant to the biomass. The flocculant can include alkylamine epichlorohydrin. The extracting can include using gravity settling or centrifugation to separate solids from the protein suspension. The salt can include magnesium sulfate. The method can include incubating the protein suspension with the support comprising PEG for 24 to 48 hours. The method can further include concentrating the protein phase to generate a product concentrate, and/or sterilizing the product concentrate to obtain a sterilized product concentrate, and/or drying the sterilized product concentrate (e.g., using a spray dryer or a freeze dryer under mild conditions).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
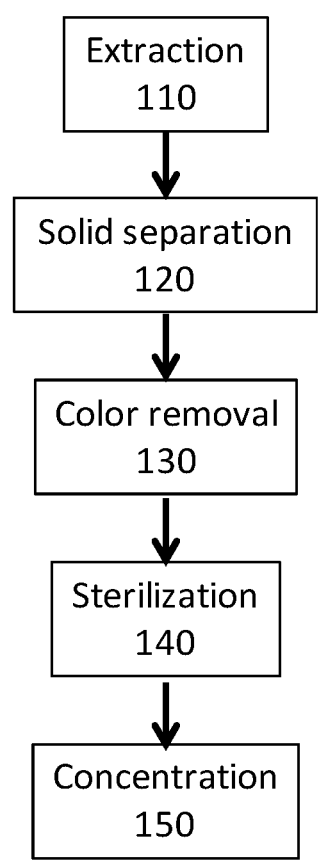
FIG. 1 is a flow diagram showing the steps in a general embodiment of an extraction and purification process as provided herein.

Low temperature-denaturing proteins in their undenatured state are critical for the success of food replica products, such as beef replica products. Existing commercial protein extraction processes however, can result in denaturation of such proteins. Further, most proteins that might have functionality in food replica products have an associated color and odor, which can detract from or inhibit their application. For example, rubisco (ribulose-1,5-bisphosphate carboxylase oxygenase), which represents about 30 to 50 percent of the soluble protein in plant chloroplasts, has a green color and a grassy odor that can inhibit its application in food replica products. Rubisco also denatures at low temperature (50° C. to 60° C.). Methods reported elsewhere for extraction of rubisco have included, for example, heat-based precipitation at 50° C. to 60° C., extraction with large concentrations of reductants, temperature based precipitation of non-rubisco proteins, carbon adsorption, crystallization based purification, and/or extraction at pH 11 followed by precipitation of the protein at pH 4.5 and extensive washing with organic solvents (see, e.g., U.S. Pat. Nos. 3,959,246, 4,006,078, 4,334,024, and 4,588,691; PCT Publication No. WO 2011/078671; Lamsal et al., *Trans. ASAE* 46(3):715-720, 2003); and Yang et al., *J. Agric. Food Chem.* 52:2223-2225, 2004).

The materials and methods provided herein can be used to extract and purify low temperature-denaturing proteins such as rubisco, in sufficient amounts and with suitable characteristics that they can be used in food replica products. These methods may provide a high purity product in as little as one step and, in some cases, without the use of chromatography. The methods also can provide the possibility of scaling up through the use of conventional extraction equipment in the chemical industry, and have low capital expenditure and increased manufacturing recovery.

The methods provided herein can include the use of a hydrophilic polymer such as polyethylene glycol (PEG). For example, a method can include a step of PEG dispersal and extraction of color bodies, followed by an aqueous two phase separation step. In some embodiments, the volume concentration of the PEG phase can be from 2% to 50% (w/v) PEG (e.g., 2-10%, 10-25%, or 25-50%), potentially salting out the protein. The affinity of color bodies to the PEG can lead to their separation from the rest of the mixture. The PEG can have a molecular weight ranging from about 300 to about 300,000 (e.g., 300, 400, 500, 1000, 2000, 3000, 4000, 5000, 6000, 7000, 8000, 9000, 10,000, 20,000, 30,000, 40,000 50,000, 60,000, 70,000, 80,000, 90,000, 100,000, 200,000, or 300,000, about 300 to about 3000, about 3000 to about 10,000, about 10,000 to about 30,000, about 30,000 to about 100,000, or about 100,000 to about 300,000). In some cases, for example, the PEG can have a molecular weight of about 8000.

In some embodiments, biomass (e.g., flowers, leaves, or other plant material) can be ground through a disintegrator and/or a high shear mixer, and then extracted with water containing PEG (e.g., mol. weight 8000 PEG) and, optionally, one or more flocculants containing alkylamine-epichlorohydrin, polydimethyldiallylammonium chloride, or polyamines (e.g., MAGNAFLOC®, SUPERFLOC®, or TRAIVIFLOC®), to form an extraction slurry. The one or more flocculants can help to reduce the amount of fine solids that carry over in the centrate and slightly reduce the color of the centrate. The presence of PEG can improve the solubility of the protein(s) and may increase the yield; PEG also has been observed to reduce the amount of fine solids carrying over in the extract.

The extraction slurry then can be decanted (e.g., using a decanter centrifuge) to separate the bulk solids from the extract. The extract can be collected in a stirred tank reactor, and salt can be added to the same to form a two-phase mixture. The salt can cause the PEG to form a discontinuous phase and separate out of the solution. Useful salts include, for example, salts of metals such as sodium, potassium, calcium, magnesium, zinc, iron, cobalt, or aluminium, with counterions such as chloride, bromide, sulfate, nitrate, acetate, cyanide, citrate, carbonate, acetate, or phosphate. In some embodiments, the salt is NaCl or $MgSO_4$. Mixtures of salts also can be used. The salt concentration can be from about 100 mM to about 2 M (e.g., 100 to 200 mM, 200 to 500 mM, 500 to 750 mM, 750 mM to 1 M, or 1 to 2 M).

Color compounds consisting of small molecules such as chlorophylls, carotenoids, flavonoids, and reaction products such as enzymatic, oxidation, or browning reaction products can be selectively retained in the PEG phase in its exclusion volume, while the proteins remain in the aqueous salt solution. Odorous compounds (e.g., grassy, green odor compounds) also can be retained in the PEG phase in its exclusion volume. The two-phase mixture then can be separated into a PEG phase and a product phase (e.g., by gravity settling or with a centrifuge, such as a disk stack centrifuge). The recovered PEG layer can be sent back to the extraction tank for the next extraction, until it is saturated with color components. At that point, the PEG phase may be heat treated to separate the pure PEG and the color bodies in solution. It is to be noted that in some embodiments, the PEG (and optional flocculant) can be added to the phase separation step, after the solid separation step.

The product phase that was separated from the two-phase mixture can be microfiltered (e.g., through a tangential flow filtration system or a one-pass dead end microfiltration system) to separate any remnant fine solids and microorganisms. The filtered product phase can be concentrated and diafiltered with water using an ultrafiltration membrane system or a combination of chromatography and an ultrafiltration membrane system, resulting in a product concentrate. This step can allow the separation of remaining PEG and salt in the filtered product phase. The product concentrate also may be subjected to a microbial reduction step, which may include, for example, pasteurization (e.g., high temperature short time pasteurization, or high pressure pasteurization), UV irradiation, or gamma irradiation. In some cases, a non-thermal method can be useful. The product concentrate (sterilized or non-sterilized) can be dried using a spray dryer or a freeze dryer or the like at mild conditions to ensure that the protein is not denatured, resulting in pure, de-colored, de-odored protein. It is noted that the product may contain low levels (e.g., less than about 1%, 0.1%, 0.01%, about 0.001%, about 0.0001%, or about 0.00001% (w/w)) of PEG.

In some embodiments, the hydrophilic polymer (e.g., PEG) does not have to physically contact the protein suspension, but may be separated from the protein suspension by a permeable membrane with a pore size small enough to prevent transfer of the polymer or the target protein. For example, the PEG and the protein suspension can be separated by a membrane having a pore size from about 3 kDa to about 500 kDa (e.g., 3 to 5 kDa, 5 to 10 kDa, 10 to 30 kDa, 30 to 50 kDa, 50 to 100 kDa, or 100 to 500 kDa). The concentration of the PEG phase can be between 2-50% (w/v) PEG (e.g., 2-10%, 10-25%, or 25-50%). The protein suspension can contain one or more salts to promote the transfer of the colored bodies and off-flavor compounds. In some embodiments, the pH of the protein solution also can be adjusted (e.g., to a pH between 2 and 10) to promote the transfer of colored and off-flavor compounds. As above, the protein suspension can include a salt such as, without limitation, a salt of a metal such as sodium, potassium, calcium, magnesium, zinc, iron, cobalt, or aluminium, with counterions such as chloride, bromide, sulfate, nitrate, acetate, cyanide, citrate, carbonate, acetate, or phosphate (e.g., NaCl or $MgSO_4$), or a mixture of salts. Again, the salt concentration can range from about 100 mM to about 2 M. The affinity of the color bodies for PEG can lead to their separation from the rest of the mixture. As above, the PEG can have a molecular weight ranging from about 300 Da to about 300,000 Da (e.g., about 8000 Da). The use of PEG to indirectly pull off colored bodies and off-flavor compounds may be particularly useful for proteins that can precipitate at low PEG concentrations (thus rendering subsequent phase separation problematic). For example, PEG may be utilized across a membrane to remove off-flavors from, without limitation, soy 7S and pea albumin proteins.

The use of a membrane to keep the protein suspension separate from the PEG phase can eliminate the need for a phase separation step. The protein and PEG suspensions can be contacted with a permeable membrane using a variety of methods, such as dialysis, transflow filtration, ultrafiltration, microfiltration, or nanofiltration. The membrane can be made from any of a variety of materials, including polymers such as polyethersulfone, polypropylene, polyvinylidene fluoride, polyacrylonitrile, cellulose acetate, and polysulfone. In some embodiments, the membranes can be incorporated into a physical matrix such as ceramic or steel.

In some embodiments involving the use of a membrane, biomass (e.g., flowers, leaves, or other plant material) can be ground through a disintegrator and/or a high shear mixer, and then extracted with water containing one or more flocculants (e.g., MAGNAFLOC®, SUPERFLOC®, or TRAMFLOC®) to form an extraction slurry. The flocculant can help reduce the amount of fine solids that carry over in the centrate, and also can reduce the color of the centrate. The extraction slurry then can be decanted using a decanter centrifuge or passed through a screw press unit to separate the bulk solids and the centrate. The centrate can be microfiltered through a tangential flow filtration system or a one-pass dead end microfiltration system to remove any remnant fine solids and microorganisms. The microfiltration permeate can be collected in a tank and salt can be added to attain a certain conductivity. This solution then can be diafiltered with a UF membrane against an 8% PEG solution. Once the product is decolorized, the PEG diafiltration can be stopped, and the resulting material can be is concentrated and diafiltered with water to obtain low salt, concentrated, decolorized protein (e.g., Rubisco). In some embodiments, the sample can be centrifuged to remove solids. The product concentrate also may be subjected to a microbial reduction step, which may include, for example, pasteurization (e.g., high temperature short time pasteurization, or high pressure pasteurization), UV irradiation, or gamma irradiation. In some cases, a non-thermal method can be useful. The product concentrate then can be dried using a spray dryer, a freeze dryer, or the like under mild conditions to ensure that the protein is not denatured, thus resulting in pure, decolored, deodored protein.

In some embodiments, the hydrophilic polymer can be immobilized before being contacted by a protein suspension. Again, biomass (e.g., flowers, leaves, or other plant material) can be ground using a disintegrator and/or a high shear mixer, and one or more flocculants containing alkylamine-epichlorohydrin, polydimethyldiallylammonium chloride, or polyamines (e.g., MAGNAFLOC®, SUPERFLOC®, or TRAMFLOC®) optionally can be added to form an extraction slurry, and the suspension optionally can be clarified to remove solids, such as by decantation, settling, or centrifugation. The suspension of proteins then can be exposed to an immobilized hydrophilic polymer (e.g., PEG). In some embodiments, immobilized PEG may be present in the form of a resin. The resin can be constructed of a solid core that has a coating of PEG molecules. The solid core can contain any of a variety of materials, such as SEPHAROSE®, agarose, polycarbonate, hydroxyapatite, glass, metal, charcoal, silica, alumina, ceramics, polypropylene, polystyrene, or divinylbenzene. As above, the PEG can have a molecular weight ranging from about 300 Da to about 300,000 Da (e.g., about 8000 Da). In some embodiments, the PEG can be immobilized by crosslinking to form a resin such as NovaPEG (EMD Millipore; Billerica, Mass.). In other embodiments, the PEG can be immobilized on a membrane. As for the protocols described above, the protein suspension can contain one or more salts to promote the transfer of the colored bodies (e.g., salt present in the range of 100 mM to 2 M, including salts of metals such as sodium, potassium, calcium, magnesium, zinc, iron, cobalt, or aluminium, with counterions such as chloride, bromide, sulfate, nitrate, acetate, cyanide, citrate, carbonate, acetate, or phosphate).

In some embodiments of methods utilizing an immobilized hydrophilic polymer (e.g., PEG), a protein suspension can be exposed to the polymer on a resin by addition of the resin to the suspension. After a period of time sufficient to allow the colored bodies to associate with the PEG (e.g., 1 minute to 48 hours, such as 1 to 10 minutes, 10 to 30 minutes, 30 to 60 minutes, 60 minutes to 2 hours, 2 to 4 hours, 4 to 6 hours, 6 to 12 hours, 12 to 24 hours, or 24 to 48 hours) at 4° C. to 45° C. (e.g., 4° C. to 10° C., 10° C. to 20° C., or 20° C. to 45° C.), the protein can be separated from the immobilized PEG by a variety of methods, including gravity filtration, vacuum or centrifugal filtration, settling and decantation, or centrifugation and isolation of the centrate. The immobilized PEG optionally can be washed to remove entrained proteins.

In some embodiments, immobilized PEG can be used as a chromatography resin. A protein suspension can be passed through the bed of resin under conditions in which the colored bodies bind to the resin but the target protein flows through the bed and is collected. Again, the protein phase can contain one or more salt to promote the binding of colored bodies.

A decolorized, deodorized protein suspension can be further processed to yield a decolorized, deodorized protein powder. For example, decolorized proteins can be concentrated and diafiltered. In some embodiments, a decolorized protein suspension can be centrifuged to remove solids. The concentrate also can be subjected to a microbial reduction step. As noted above, such procedures can include pasteurization (e.g., high temperature short time pasteurization, or high pressure pasteurization), UV irradiation, or gamma irradiation, or non-thermal methods. The product concentrate then can be dried (e.g., using a spray dryer, a freeze dryer, or the like) under mild conditions to ensure that the protein is not denatured, resulting in pure, decolored, deodored proteins.

Turning now to the figures, FIG. 1 is a flow diagram depicting the general steps in an embodiment of a method as provided herein. In general, extraction step 110 (e.g., using a disintegrated/milled/homogenized biomass and a buffer) can be followed by solid separation step 120 (e.g., by decanting and addition of a flocculant, and optionally also PEG), color removal step 130 (e.g., by addition of PEG and salt, and optionally a flocculant, followed in some embodiments by chromatography, pH precipitation, and resolubilization), sterilization step 140 (e.g., by microfiltration, pasteurization, or UV irradiation), and concentration step 150 (e.g., by ultrafiltration or thin film evaporation, followed by drying).

FIG. 2 is a flow diagram depicting the steps in an exemplary embodiment of an extraction and purification method as provided herein. Protein rich solids are subjected to disintegration step 210, followed by extraction 220 with an aqueous solution containing PEG and, optionally, one or more flocculants. Solids are separated out in step 230. Salt is added to the extract (e.g., via recycling step 265), and phase separation step 240 separates PEG from the protein product phase. The PEG is recycled in step 245 for use in future extraction steps. The protein product phase is subjected to filtration step 250, followed by concentration step 260, during which salt is removed and recycled via step 265 for use in future phase separation steps. The concentrated protein product is subjected to sterilization step 270 and drying step 280, to yield a non-denatured, decolorized, deodorized protein product. An example of the use of this method is provided in Example 1 below.

Figure 2A:
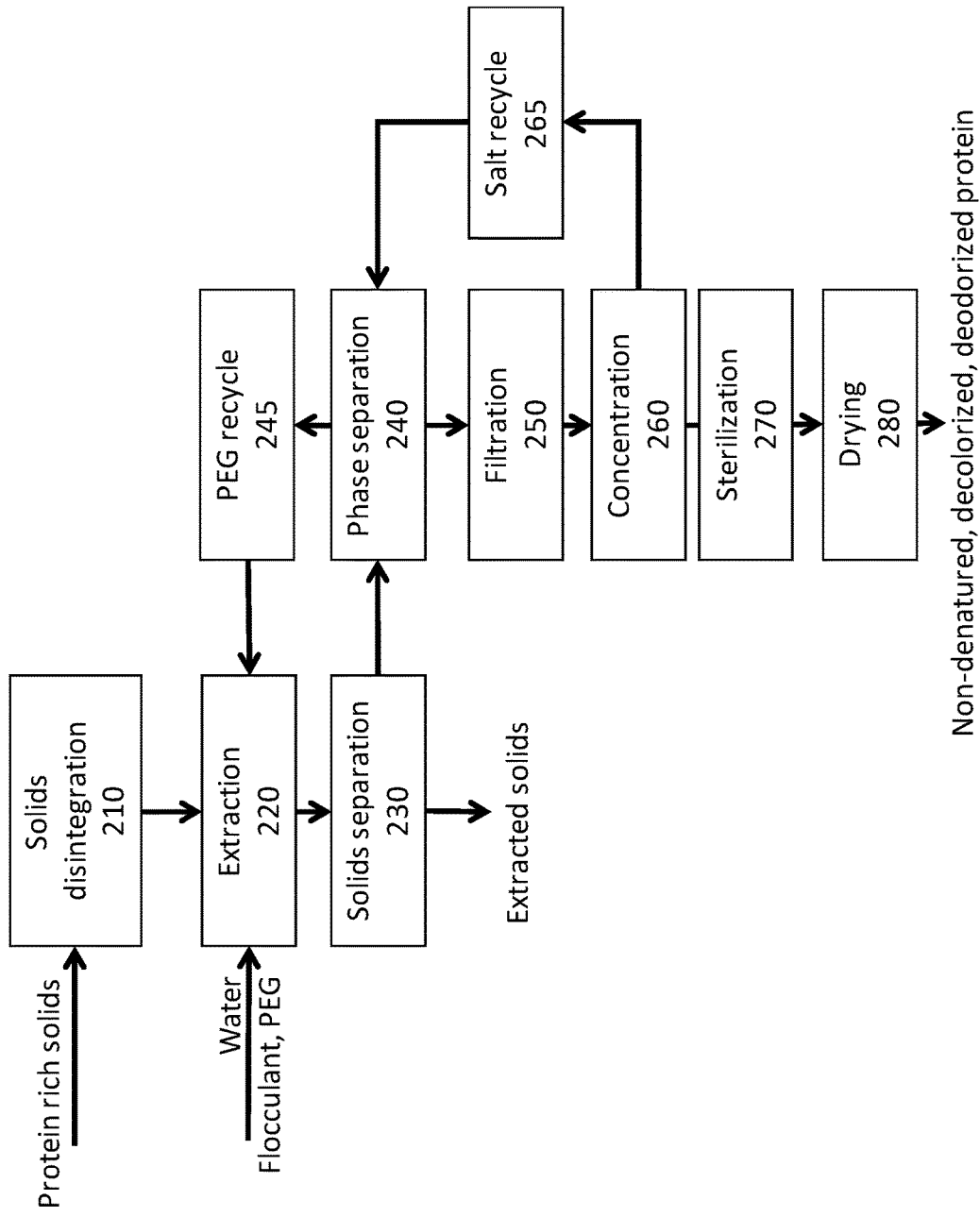
FIG. 2A is a flow diagram showing the steps in an embodiment of an extraction and purification process as provided herein.
Figure 2B:
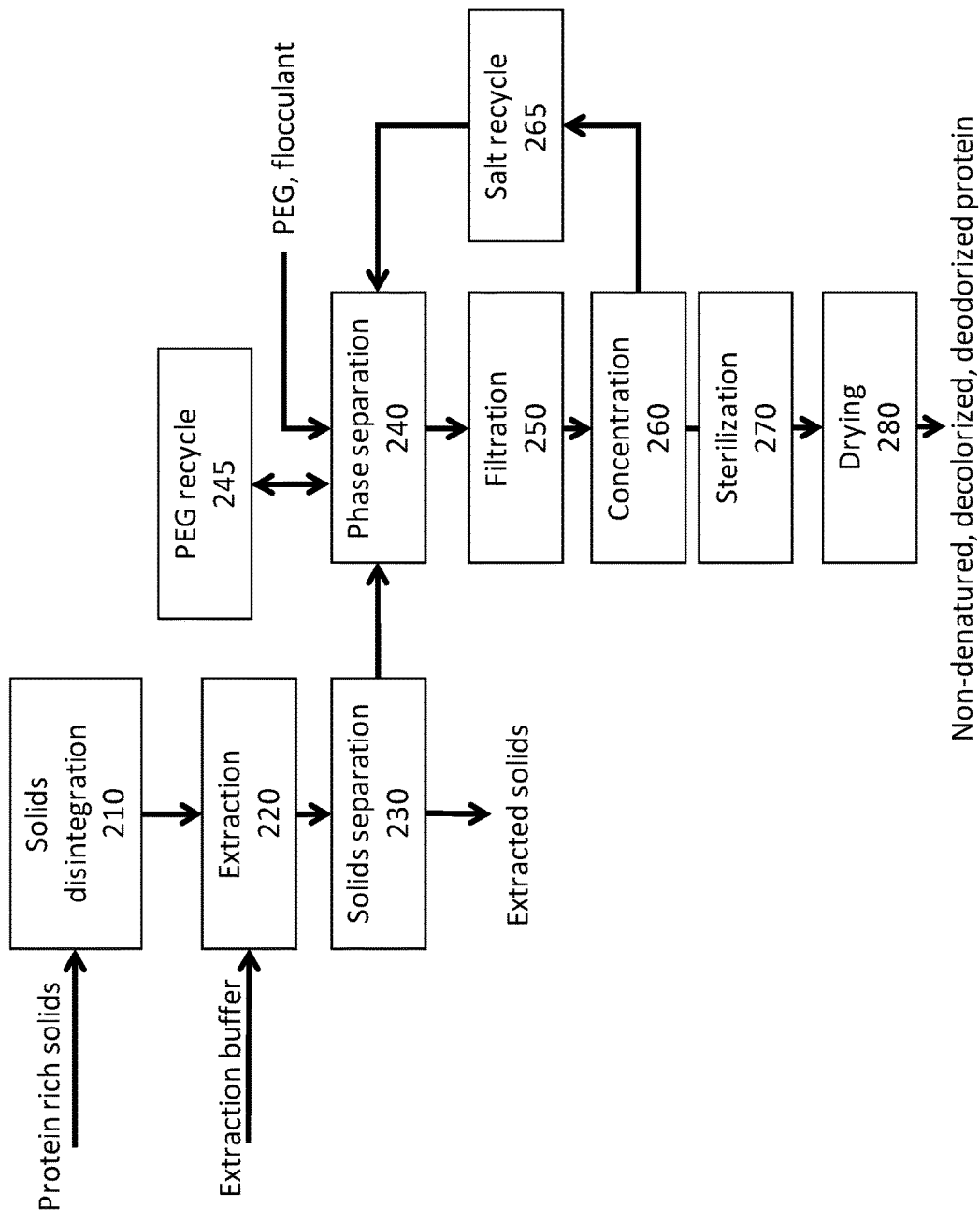
FIG. 2B is a flow diagram depicting an alternate embodiment of the process depicted in FIG. 2A.

FIG. 2B is a flow diagram showing the steps in an alternative embodiment of the method depicted in FIG. 2A. In this embodiment, the PEG is added to phase separation step 240, optionally with a flocculant, and the PEG is recycled to further phase separation steps.

Figure 3:
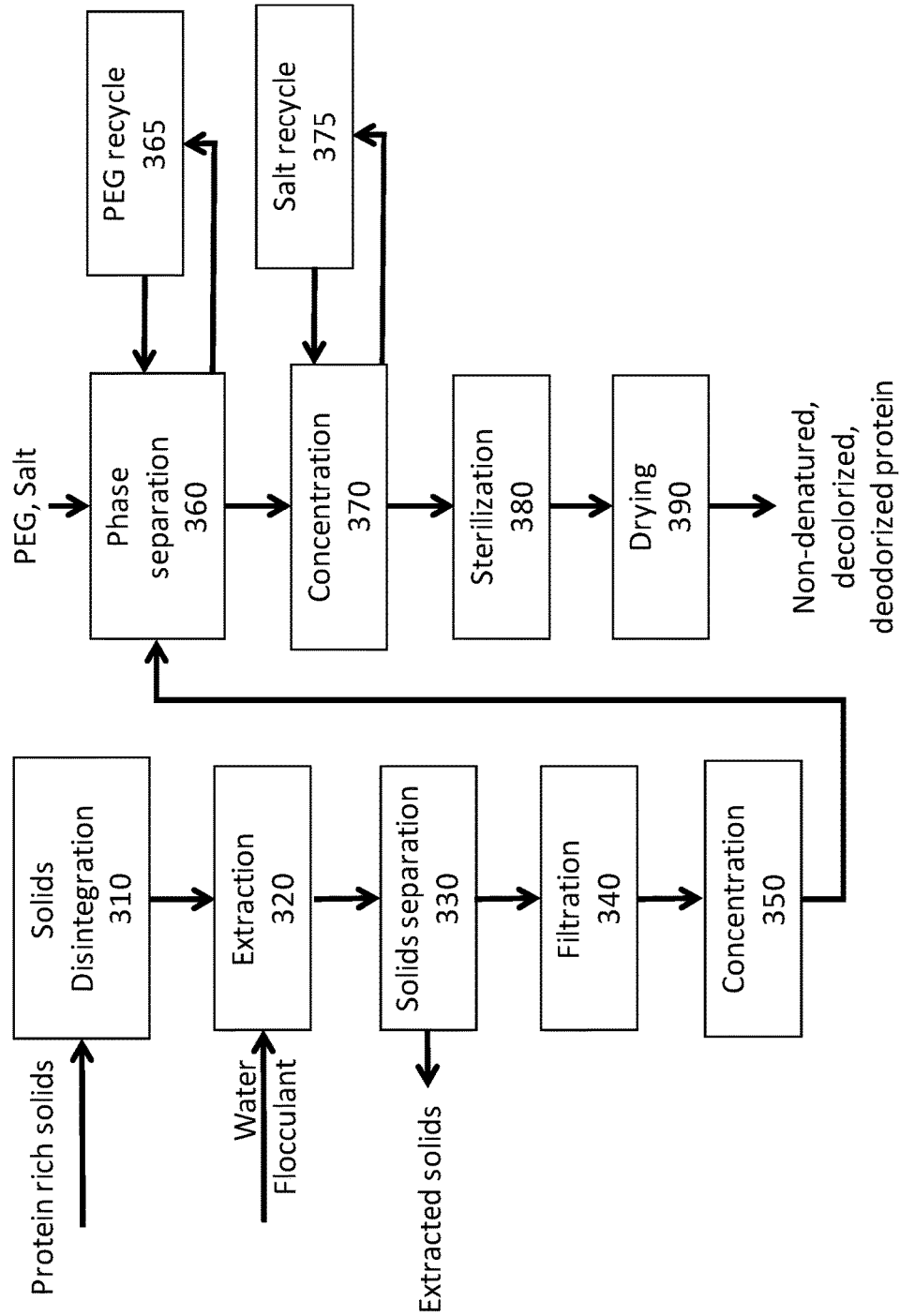
FIG. 3 is a flow diagram showing the steps in another embodiment of an extraction and purification process as provided herein.

FIG. 3 is a flow diagram depicting the steps in another embodiment of an extraction and purification process as provided herein, in which PEG is added after the initial extracting step. Protein rich solids are subjected to disintegration step 310, followed by extraction step 320 with an aqueous solution that optionally contains one or more flocculants. Solids are separated in step 330, and the extract is filtered and concentrated in steps 340 and 350, respectively. PEG and salt are added to generate a multi-phase mixture. The phases are separated in step 360. The PEG is recycled in step 365 for use in future separation steps. The protein product phase is concentrated in step 370, during which salt is removed and recycled in step 375 for use in future phase separation and/or concentration steps. The concentrated protein product is subjected to sterilization step 380 and drying step 390, resulting in a non-denatured, decolorized, deodorized protein.

Figure 4:
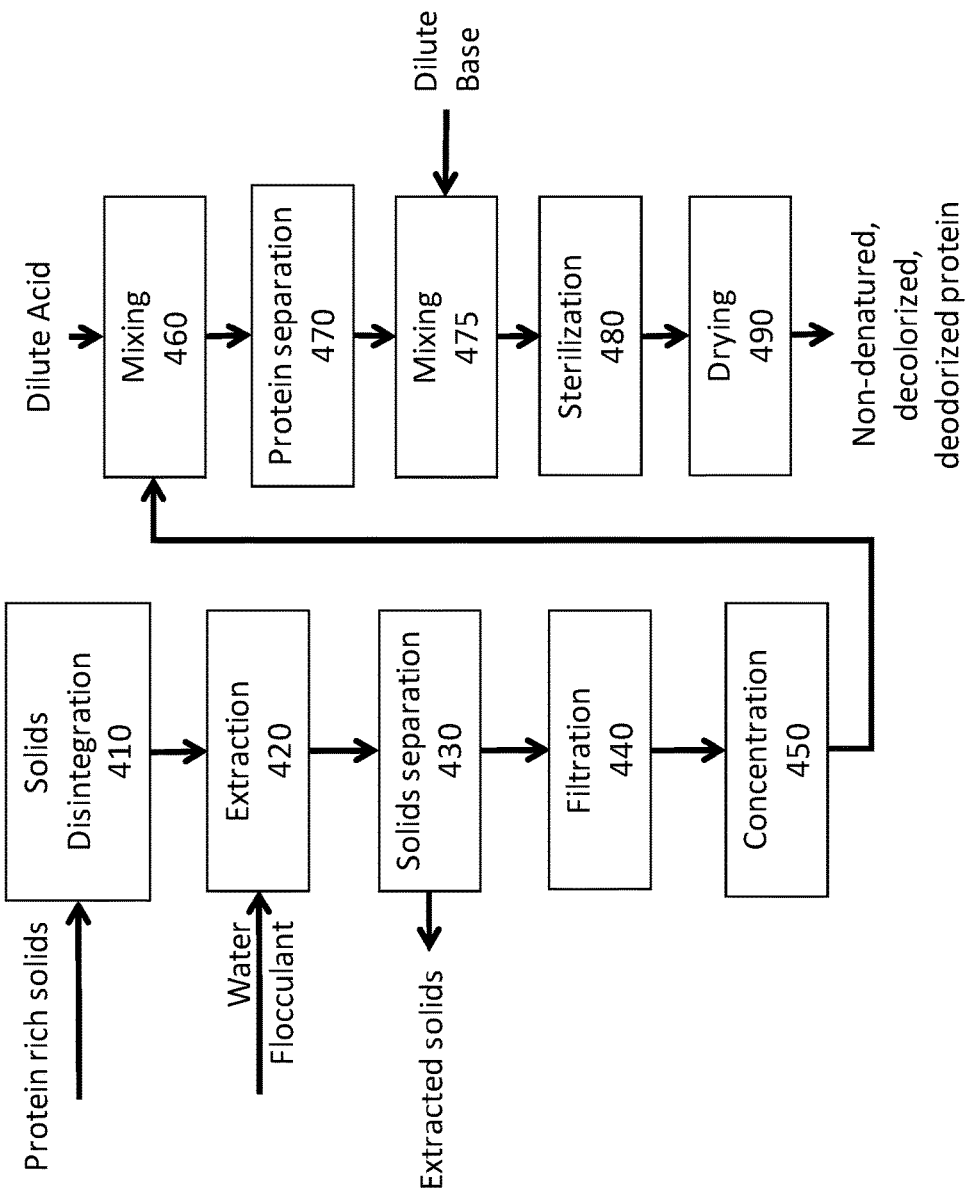
FIG. 4 is a flow diagram showing the steps in an embodiment of a pH based purification process.

FIG. 4 is a flow diagram depicting the steps in an embodiment of a pH based purification process. Protein rich solids are subjected to disintegration step 410, followed by extraction step 420 with added extraction buffer (e.g., an aqueous solution that optionally contains a flocculant). Solids are separated in step 430, and the remaining solution is filtered in step 440, and concentrated in step 450. Dilute acid is mixed with the concentrate in step 460, and the protein is separated out in step 470. Dilute base is mixed with the protein in step 475, after which the protein product is subjected to sterilization step 480 and drying step 490. An example of the use of this method is provided in Example 3 below.

Figure 5:
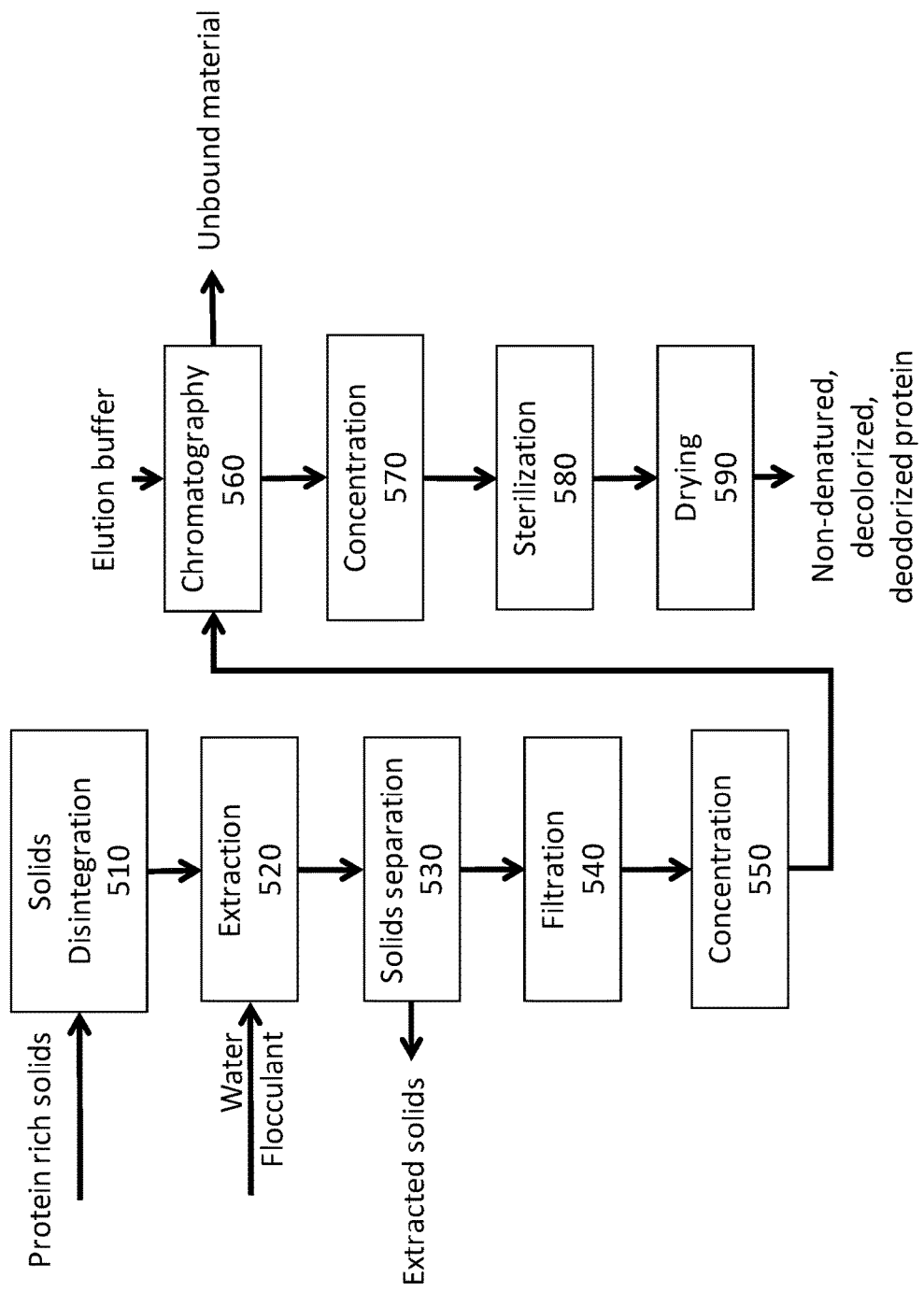
FIG. 5 is a flow diagram showing the steps in an embodiment of a chromatographic purification process.

FIG. 5 is a flow diagram depicting the steps in an embodiment of a chromatography purification process. Protein rich solids are subjected to disintegration step 510, followed by extraction step 520 with extraction buffer (e.g., an aqueous solution that optionally contains a flocculant). Solids are separated in step 530, and the remaining solution is filtered in step 540, and concentrated in step 550. The concentrate is applied to a chromatography column (e.g., a gel filtration column) in step 560, and non-protein and unbound material is washed out. The protein is eluted and then concentrated in step 570, after which the concentrated protein product is subjected to sterilization step 580 and drying step 590. An example of the use of this method is provided in Example 4 below.

Figure 6:
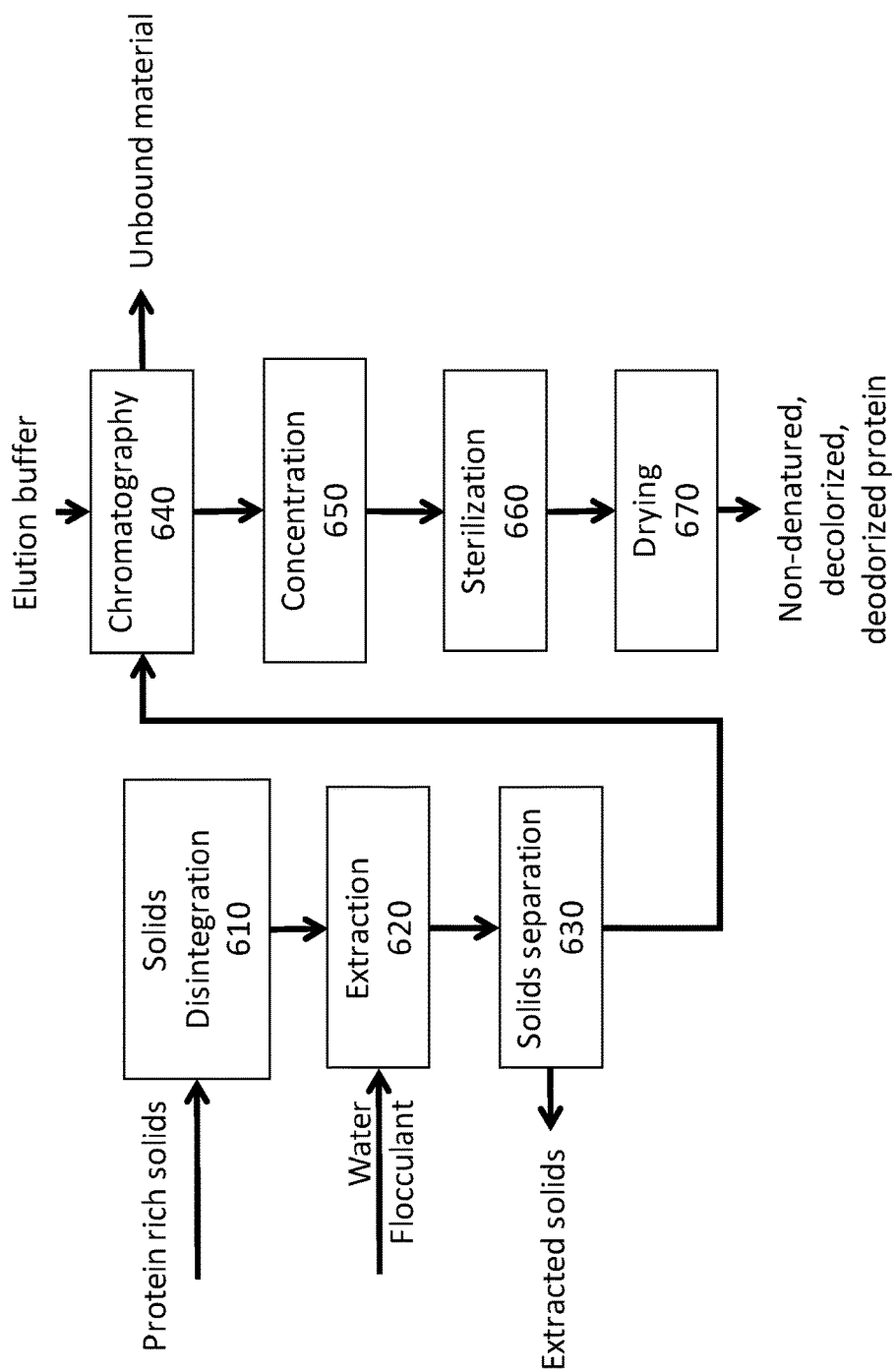
FIG. 6 is a flow diagram showing the steps in an embodiment of an expanded bed chromatographic purification process.

FIG. 6 is a flow diagram depicting the steps in an embodiment of an expanded bed chromatographic purification method. Protein rich solids are subjected to disintegration step 610, followed by extraction step 620 with added extraction buffer (e.g., an aqueous solution that optionally contains a flocculant). Solids are separated in step 630. The remaining solution is applied to a chromatography column (e.g., an ion exchange column, or a hydrophobic interaction or pure adsorption-based system such as activated carbon) in step 640, and non-protein and unbound material is washed out. The protein is eluted and then concentrated in step 660, after which the concentrated protein product is subjected to sterilization step 670 and drying step 680.

Figure 7:
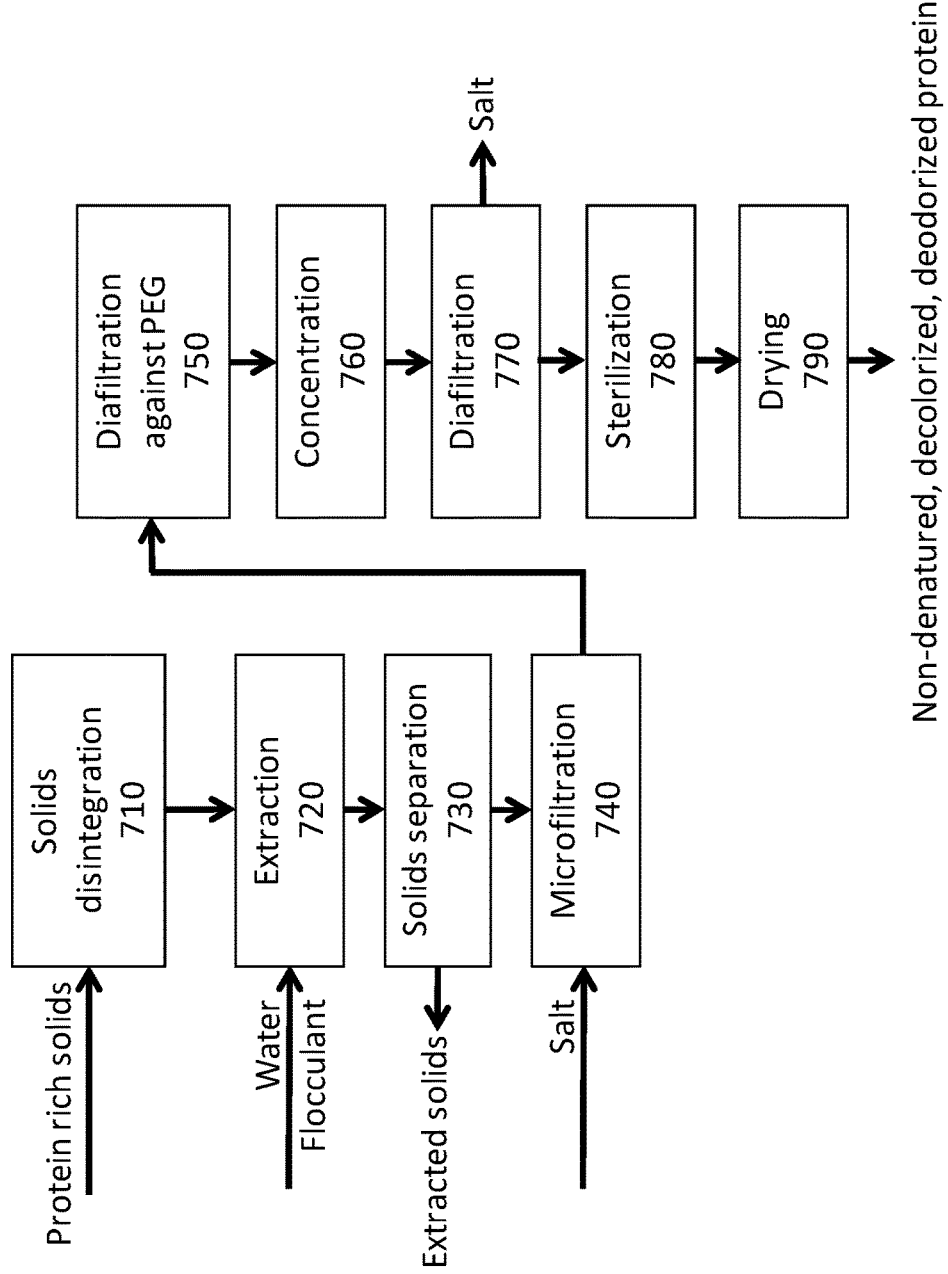
FIG. 7 is a flow diagram showing the steps in an embodiment of a purification process utilizing a membrane.

FIG. 7 is a flow diagram illustrating the steps in an embodiment of a method in which a membrane is used to keep the protein suspension separate from the PEG solution. Protein-rich solids are subjected to disintegration step 710, followed by extraction step 720 with water and optional flocculant. Solids are removed in step 730, and microfiltration step 740 is used to remove fine remnant solids and/or microorganisms. In step 750, the filtrate is diafiltered against PEG across a membrane, a step that can include dialysis, transflow filtration, ultrafiltration, microfiltration, or nanofiltration, for example. The protein solution then is concentrated in step 760, diafiltered to remove salt in step 770, and subjected to sterilization step 780 and drying step 790.

Figure 8:
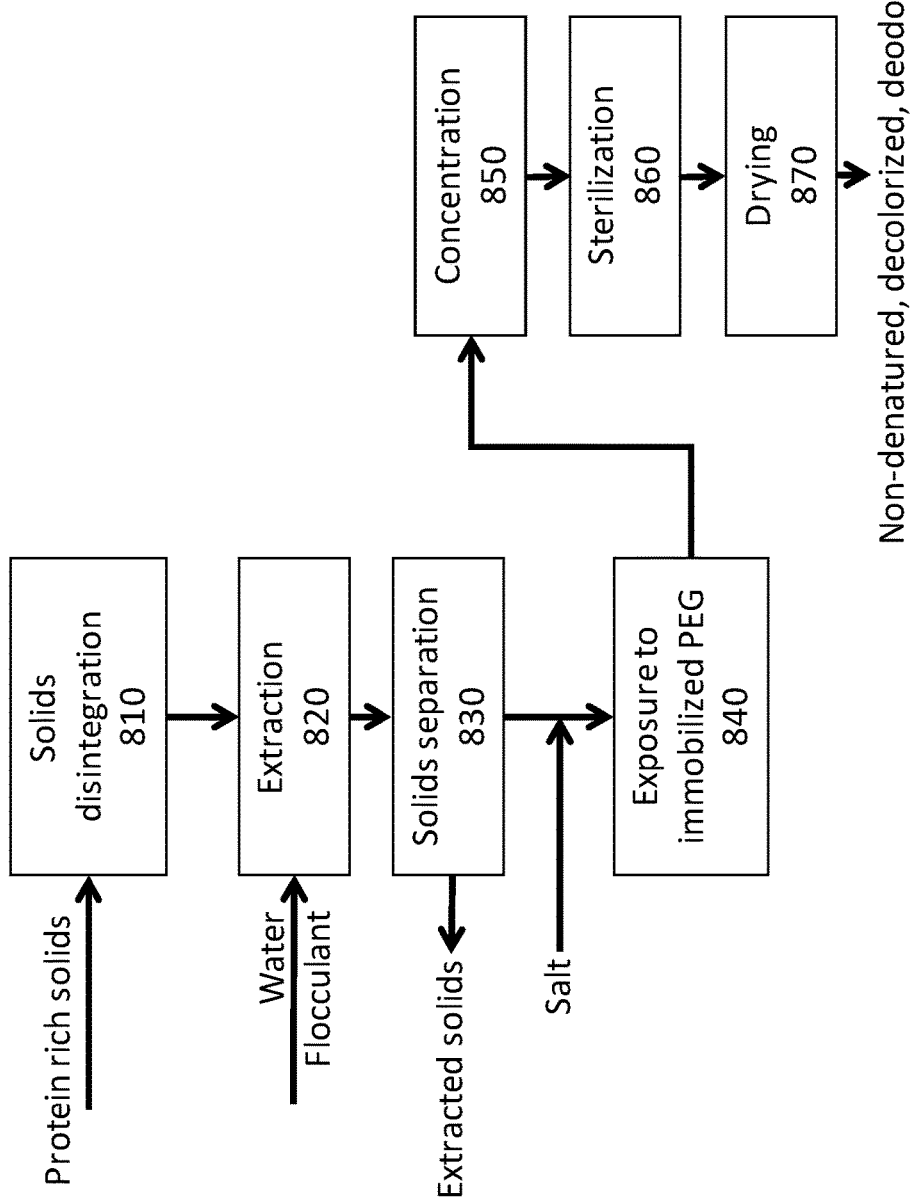
FIG. 8 is a flow diagram showing the steps in an embodiment of a purification process utilizing immobilized PEG.

FIG. 8 is a flow diagram illustrating the steps in an embodiment of a method in which a colorants and odorous compounds are removed using immobilized PEG. Protein-rich solids are subjected to disintegration step 810, followed by extraction step 820 with water and optional flocculant. Solids are removed in step 830, and the protein suspension is added to immobilized PEG (e.g., in a chromatography column or as a batch chromatography step) and incubated in step 840. In step 850, the protein solution is concentrated, followed by sterilization step 860 and drying step 870.

Figure 9:
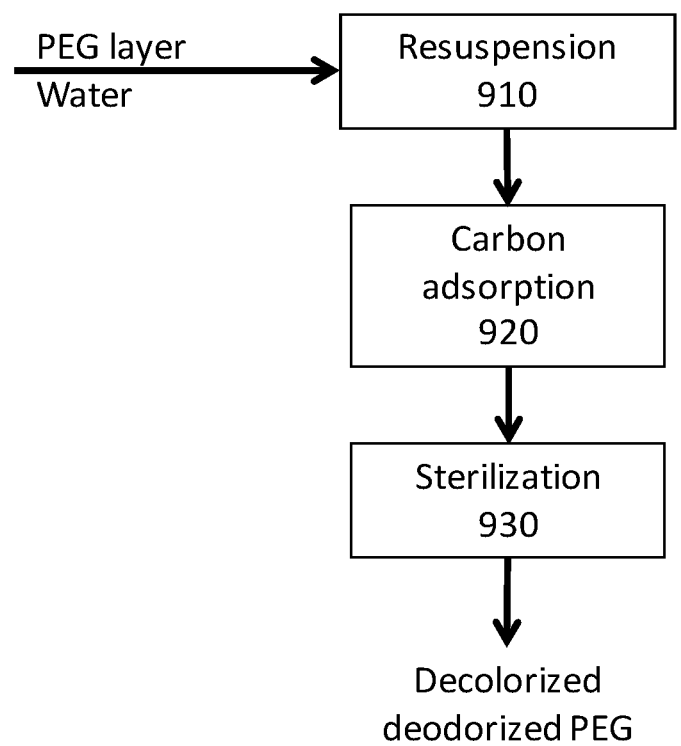
FIG. 9 is a flow diagram showing the steps in an embodiment of a PEG recycling process.

FIG. 9 is a flow diagram depicting steps in an embodiment of a PEG recycling process. After addition of PEG and phase separation (e.g., as depicted in FIGS. 2 and 3 and described above), the PEG in the PEG layer can be resuspended in step 910, and then subjected to carbon adsorption step 920. The PEG can optionally be sterilized in step 930 (e.g., by microfiltration, pasteurization, or UV irradiation).

Figure 10:
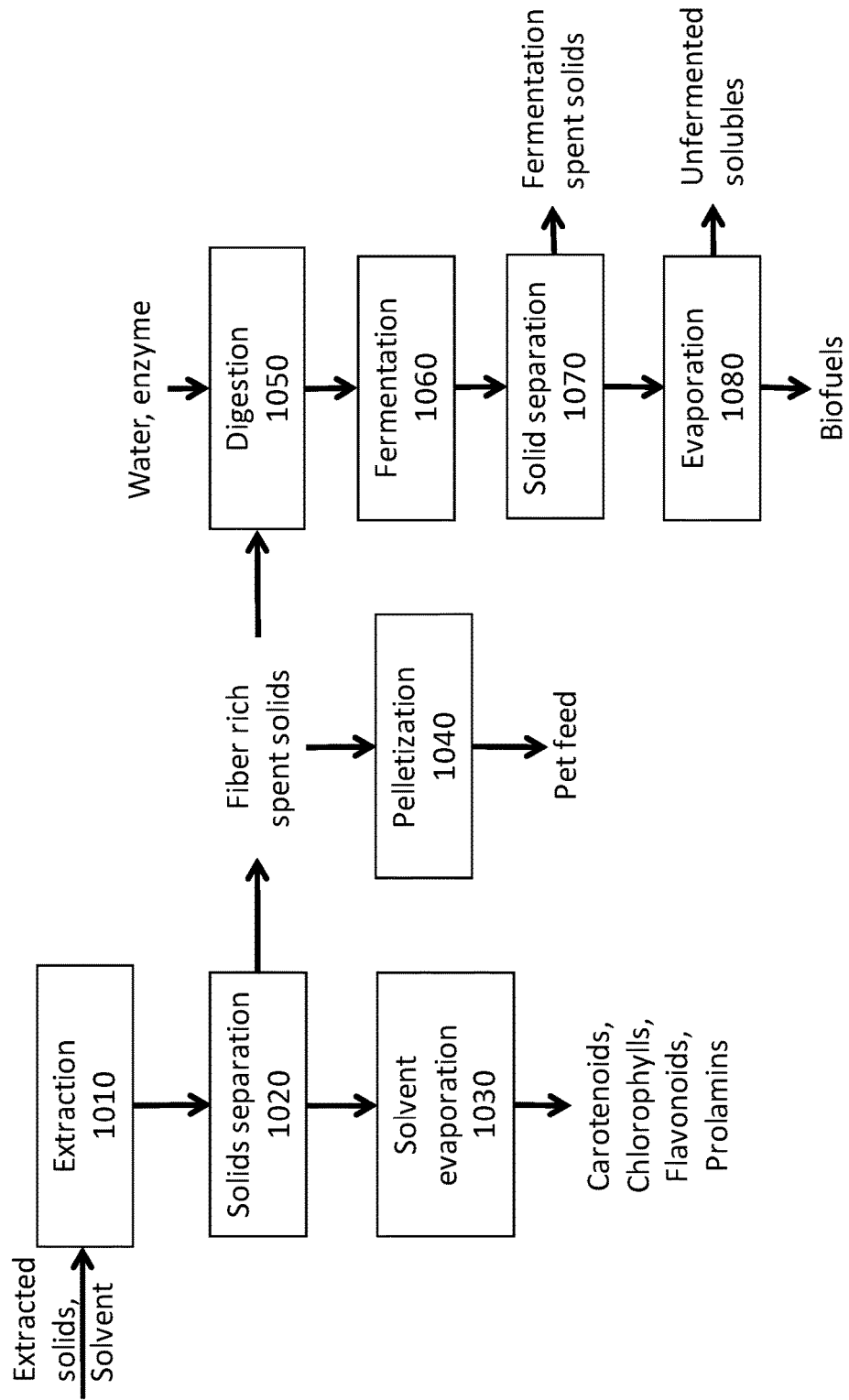
FIG. 10 is a flow diagram showing the steps in another embodiment of an extraction and purification process as provided herein, indicating possible added value steps.

FIG. 10 is a flow diagram showing steps in an embodiment of an extraction and purification method as provided herein, with the inclusion of value added steps. Extracted solids and solvent from a separation step (e.g., in a PEG based method as described herein) are subjected to extraction step 1010, followed by separation step 1020. The solvent is evaporated in step 1030 to yield compounds such as carotenoids, chlorophylls, flavonoids, and prolamins. Fiber rich, spent solids are pelleted in step 1040 and used in products such as pet feed, for example, or are subjected to enzyme digestion step 1050, followed by fermentation step 1060 and solid separation step 1070. Fermented, spent solids are removed. The solvent is evaporated in step 1080, yielding unfermented soluble compounds, and other materials that can be used as biofuels, for example.

The invention will be further described in the following examples, which do not limit the scope of the invention described in the claims.

EXAMPLES

Example 1—Spinach Rubisco Isolation

One kg of fresh spinach leaves were macerated in a VITA-PREP® 3 blender (Vitamix Corp., Cleveland, Ohio) in a ratio of 1:1 (w/w) with potassium phosphate buffer (pH 7.4) containing 8% (w/v) PEG (Carbowax Sentry PEG 8000; Dow Chemicals, Midland, Mich.) and 0.1% (w/v) cationic flocculant (863A; Tramfloc, Inc., Houston, Tex.). The extraction was performed for 3 minutes at the highest setting (3HP motor) maintaining the temperature at less than 30° C. at all times. The pH was adjusted to 7.4 post-grinding, using a 10 M NaOH solution. The homogenate was centrifuged at 3500 g for 5 minutes using a bench top centrifuge (Allegra X15R, SX4750 rotor; Beckman Coulter, Inc., Pasadena, Calif.). The pellet was discarded and the supernatant (about 1.6 L) was collected separately. Magnesium sulfate heptahydrate salt (K+S KALI GmbH, Kassel, Germany) was added to the supernatant to attain 1M concentration. The solution was mixed thoroughly and centrifuged at 5451 g for 3 minutes using a bench top centrifuge (Allegra X15R, SX4750 rotor; Beckman Coulter, Inc.). Three layers formed in the centrifuge bottle, and the remaining green solids separated out as a pellet (about 0.1 L). The PEG layer (about 0.3 L) separated and formed the top layer, selectively fractionating the color compounds and odorous compounds. A clear product protein remaining in the middle layer was then microfiltered using a 0.2 µm modified polyethersulfone (mPES) membrane in a hollow fiber format (KROSFLO® K02E20U-05N; Spectrum Laboratories, Inc., Rancho Dominguez, Calif.). The retentate (about 0.25 L) was diafiltered using about 0.75 L of 1M magnesium sulfate solution. The permeate from this filtration step (about 3 L) was concentrated using a 70 kDa mPES membrane (MiniKros NO2E070-05N; Spectrum Laboratories, Inc.) to about 0.1 L. This was further diafiltered with about 0.5 L DI water in 5 steps. The protein concentrate had a pH of about 7 and conductivity less than 5 mS/cm. The resulting protein concentrate was clear pale yellow. The product was dried using a spray dryer, or frozen and dried using a freeze dryer. This material was analyzed using the standard 660 nm Pierce protein assay and SDS gel densitometry. The dry solids were analyzed using the IR moisture analyzer. The flocculant and PEG concentration in the final product were analyzed using titration methods. The protein concentration was about 91% (w/w), and the total solids about 95% (w/w). The PEG and flocculant concentrations were analyzed at less than 0.2% (w/w). The product was over 90% pure with over 90% recovery through the process. The product obtained was decolored and retained the low temperature denaturation property.

Example 2—Alfalfa Rubisco Isolation

Two thousand L of extraction buffer (potassium phosphate at pH 7.4) was prepared in a jacketed stirred tank containing 8% (w/v) PEG (Carbowax Sentry PEG8000; Dow Chemicals) and 0.1% (w/v) cationic flocculant (863A; Tramfloc, Inc.). Five hundred kg of fresh alfalfa leaves were macerated in a Corenco M12DA disintegrator (Corenco, Santa Rosa, Calif.) with continuous recirculation of the extraction buffer during grinding to improve the disintegration and maintaining the process temperature to less than 40° C. at all times. The pH was adjusted to 7.4 post-grinding, using a 10 M NaOH solution. The homogenate was centrifuged at 3500 g with a GEA Westfalia decanter GCE-345 (GEA Mechanical Equipment, New Jersey, N.J.) at a feed rate of about 5 gallons per minute (gpm). The pellet was discarded. About 625 kg magnesium sulfate salt (K+S KALI GmbH), was added to the liquid centrate (about 2200 L). The solution was mixed thoroughly and centrifuged with a GEA Westfalia separator ESD-30 (GEA Mechanical Equipment) at a feed rate of about 5 gpm. The green solids were ejected out as a pellet, losing about 10% (v/v) of the feed. The PEG layer (about 20% v/v of the feed) separated and formed the top layer selectively fractionating the color compounds and odorous compounds. A clear product protein remaining in the middle layer was then microfiltered using a 0.2 µm modified mPES membrane in a hollow fiber format (KROSFLO® K02E20U-05N; Spectrum Laboratories, Inc.). The retentate (about 200 L) was diafiltered using about 400 L of 1 M magnesium sulfate solution. The permeate from this filtration step was concentrated using a 70 kDa mPES membrane (KROSFLO® KM-070E-300-01N; Spectrum Laboratories, Inc.) to about 50 L. This was further diafiltered with about 250 L DI water in 5 steps. The protein concentrate had a pH of about 7 and conductivity less than 5 mS/cm. The resulting protein concentrate was clear pale yellow. The product was dried using a spray dryer, or frozen and dried using a freeze dryer. This material was analyzed using the standard 660 nm Pierce protein assay and SDS gel densitometry. The dry solids were analyzed using the IR moisture analyzer. The protein concentration was about 880 g/L and the total solids about 95% (w/w). The PEG and flocculant concentrations were analyzed at less than 0.2% (w/w). The product was over 90% pure, with over 90% recovery through the process. The product obtained was decolored and retained the low temperature denaturation property.

Example 3—Spinach Rubisco Isolation Using pH Based Purification

One kg of fresh spinach leaves was macerated in a "Vitamix" bender at a ratio of 1:1 with potassium phosphate buffer (pH 7.4) containing 0.1 M NaCl. The pH was adjusted to 7.4 post grinding using 10 M NaOH solution. The homogenate was centrifuged at 3500 g for 5 minutes. The solids pellet was discarded, and the liquid centrate (about 1.6 L) was then microfiltered using a 0.2 um mPES membrane. The retentate was diafiltered using about 1.5 L of the extraction buffer. The permeate from this filtration step (~3 L) was concentrated using a 10 kDa mPES membrane to about 0.1 L. The protein concentrate at this step was at about pH 7.4. An acid (e.g., HCl) was added to the concentrate to decrease the pH to 5. The concentrate mixture was stirred vigorously for 30 minutes using a magnetic stir plate or a homogenizer. This mixture was then centrifuged at 3500 g for 5 minutes to obtain an off white pellet and a brown centrate. The supernatant was discarded and the protein pellet was washed with deionized water. The pellet was resuspended in 0.05-0.1 L DI water. The solution was mixed vigorously into a uniform slurry and the pH was slowly raised to 11 using a base (e.g., NaOH). The solution was clear yellow. The pH was then reduced to 9 to maintain the clear mixture. The product was dried using a spray dryer in this form, or frozen and dried using a freeze dryer. The product obtained was slightly decolored, and retained the low temperature denaturation property.

Example 4—Spinach Rubisco Isolation Using Chromatography

The concentrate prepared in Example 3 above was purified by size exclusion chromatography. A Superdex 200 column (26/600) was pre-equilibrated with 20 mM KPhos pH 7.4, 100 mM NaCl. About 0.4 g protein (5 ml concentrate) was injected onto the column at 2.5 ml/min. The column was then eluted with 20 mM KPhos pH 7.4, 100 mM NaCl buffer. A high-resolution separation between the agglomerated protein in the interstitial volume, pure Rubisco, color components (pink, yellow), and salt was observed.

Example 5—Spinach Rubisco Decolorization by Diafiltration

One hundred grams of fresh spinach leaves were macerated in a VITA-PREP® 3 blender (Vitamix Corp.; Cleveland, Ohio) in a ratio of 1:4 (w/w) with DI water. The extraction was performed for 3 minutes at the highest setting (3HP motor), maintaining the temperature at less than 30° C. at all times. The pH was adjusted to 7.4 post-grinding, using 10 M NaOH. The homogenate was centrifuged at 10000 g for 30 minutes using a bench top centrifuge (Allegra X15R, SX4750 rotor; Beckman Coulter, Inc., Pasadena, Calif.). The pellet was discarded and the supernatant was collected separately. Sodium chloride salt was added to the supernatant to attain 0.75M concentration. The solution was then dialyzed against 8% PEG (Carbowax Sentry PEG 8000; Dow Chemicals, Midland, Mich.) solution with a 3 kDa UF membrane.

The color permeated through the membrane into the PEG phase, along with some protein and water. The product at the end of dialysis was 2× concentrated with no color. This material was analyzed using a standard 660 nm Pierce protein assay and SDS gel densitometry.

Example 6—Spinach Rubisco Decolorization by Batch Chromatography

One hundred grams of fresh spinach leaves were macerated in a VITA-PREP® 3 blender (Vitamix Corp.; Cleveland, Ohio) in a ratio of 1:4 (w/w) with DI water. The extraction was performed for 3 minutes at the highest setting (3HP motor), maintaining the temperature at less than 30° C. at all times. The pH was adjusted to 7.4 post-grinding, using a 10 M NaOH solution. The homogenate was centrifuged at 10000 g for 30 minutes using a bench top centrifuge (Allegra X15R, SX4750 rotor; Beckman Coulter, Inc., Pasadena, Calif.). The pellet was discarded and the supernatant was collected separately. To the suspension was added 20 mg dry NovaPEG Wang resin (EMD Milipore, Cat. No. #855122) per mL of suspension. The material was then tumbled to ensure agitation for 45 hours, after which the material was centrifuged at 10000×g for 5 minutes. The supernatant was separated, and UV-VIS analysis showed significantly reduced absorbance at 320 nm. Analysis of the protein content and composition of the supernatant, by standard 660 nm Pierce protein assay and SDS gel densitometry, showed no significant change from the initial protein suspension.

Example 7—Removal of Off-Flavors from Soy Proteins by Diafiltration Against PEG

A 3% (w/v) solution of soy conglycinin was brought to pH 8.5 using 2 N NaOH. The sample was then brought to 0.75 M sodium chloride, and dialyzed against a solution of 5% PEG 8000 (pH adjusted to 8.5) containing 0.75 M sodium chloride, using a 3500 Da cut-off membrane. After dialysis against PEG plus salt, the protein sample was dialyzed against water to remove excess salt. After 20-fold reduction in salt concentration, the sample was evaluated for taste. Tasters described the final sample to be bitter but completely depleted of cardboard and earthy off-flavors. In comparison, tasters described the untreated soy conglycinin sample to be bitter and to have strong cardboard and muddy flavors.

Example 8—Variations of the Methods

Other variations of the methods described above can be used, as follows:

Process Variations

An alternative is to add the PEG after the decanting step, thereby minimizing the loss of PEG through the decanted solids. In this case, the decanter centrate is added to a preformed two phase PEG-salt solution to fractionate the color bodies in the PEG phase.

Another option is to add solid PEG to the centrate, and upon completion of mixing, add the salt to create the phase split.

An additional alternative to the process is to utilize the two-phase extraction strategy on the UF concentrate rather than the extract. In this case, the entire process is run without addition of PEG or magnesium sulfate until the UF concentrate is produced.

Another option is to centrifuge the PEG-treated solution to remove any precipitates before pasteurization or drying.

Unit Operation Variations

The disintegration and cell disruption is enhanced using a homogenizer or a high shear mill.

The disk stack-centrifuging step for separating the three layers is replaced with a step using gravity settling tanks.

The separation of the salt is performed using a desalting chromatography column, such as a G50 column.

Component Variations

The process was tested using spinach and alfalfa leaves, but it is extendable to any source of rubisco (e.g., alga, maize, wheat, rice, sorghum, rye, canola, millet, barley, soybean, sunflower, safflower, tobacco, alfalfa, potato, Brassica spp., cotton, tomato, or tobacco) or other proteins (e.g., other plant proteins).

The process can be used to remove color and/or odor from any protein suspension, including suspensions that contain one or more proteins selected from the group consisting of, without limitation, leghemoglobin, non-symbiotic hemoglobin, hemoglobin, myoglobin, chlorocruorin, erythrocruorin, neuroglobin, cytoglobin, protoglobin, truncated 2/2 globin, HbN, cyanoglobin, HbO, Glb3, and cytochromes, Hell's gate globin I, bacterial hemoglobins, ciliate myoglobins, flavohemoglobins, ribosomal proteins, actin, hexokinase, lactate dehydrogenase, fructose bisphosphate aldolase, phosphofructokinases, triose phosphate isomerases, phosphoglycerate kinases, phosphoglycerate mutases, enolases, pyruvate kinases, proteases, lipases, amylases, glycoproteins, lectins, mucins, glyceraldehyde-3-phosphate dehydrogenases, pyruvate decarboxylases, actins, translation elongation factors, histones, rubisco, ribulose-1,5-bisphosphate carboxylase oxygenase activase (rubisco activase), albumins, glycinins, conglycinins, globulins, vicilins, conalbumin, gliadin, glutelin, gluten, glutenin, hordein, prolamin, phaseolin (protein), proteinoplast, secalin, extensins, triticeae gluten, collagens, zein, kafirin, avenin, dehydrins, hydrophilins, late embyogenesis abundant proteins, natively unfolded proteins, any seed storage protein, tuber storage proteins, patatins, dioscorins, protease inhibitors, animal proteins, fish proteins, egg proteins, poultry proteins, algal proteins, fungal proteins, recombinant proteins, oleosins, caloleosins, steroleosins or other oil body proteins, vegetative storage protein A, vegetative storage protein B, moong seed storage 8S globulin, pea globulins, and pea albumins.

A higher molecular weight PEG is used to further reduce the concentration of PEG in the process.

Other hydrophilic polymers such as polypropylene glycol, butylene glycol, hexylene glycol, glycerin, diglycerin, diethylene glycol, dipropylene glycol, and mixtures thereof also are potentially useful.

Flocculants that provide the functionality of 0.05-1% v/v cationic flocculants (e.g., SUPERFLOC® 781G or MAGNAFLOC® LT 7989 from BASF, Florham Park, N.J.) are used in the extraction buffer. Other useful flocculants include, for example, lime, hydrated lime and salts of di- or trivalent metals such as ferric chloride, ferric sulfate, ferrous sulfate, aluminium sulfate, sodium aluminate, aluminium chloride, magnesium carbonate hydroxide, calcium carbonate, calcium hydroxide, activated silicates, guar gums, starches, tannins, sodium alginate, polyaluminium sulfate, polyaluminium hydroxychloride, BIO-FLOCK®, and synthetic polyelectrolytes (e.g., ZETAG®, MAGNAFLOC®, and SUPERFLOC®).

The salt used for the phase break is not limited to Epsom salt. Other useful salts include potassium phosphate, sodium chloride, and ammonium acetate. The separation is better if the ions are chosen appropriately on the Hoffmiester series; the later salts in the series can salt in the proteins.

The extraction process is modified by adding reductants such as metabisulfite (about 2% w/v solution or more) to the initial extraction buffer and maintaining anaerobic conditions through the process.

Process Efficiency

The separated PEG layer is recycled into another extraction buffer preparation, thereby maximizing the efficiency of the PEG used.

Permeate from the UF membrane separation is concentrated with an RO membrane to recover process water and salt concentrate.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for purifying a pea albumin protein, comprising:
   extracting a disintegrated pea biomass to remove solids and generate a protein suspension;
   adding salt to the protein suspension;
   adjusting the pH of the protein suspension to a pH of 2 to 10;
   dialyzing the protein suspension against a polyethylene glycol (PEG) solution, or subjecting the protein suspension to ultrafiltration using a permeable membrane to separate the protein suspension on one side of the membrane from a permeate on the other side of the membrane, wherein PEG is present on the permeate side of the membrane; and
   subjecting the dialyzed or ultrafiltered protein solution to one or more concentrating or filtering steps to generate a product phase that contains the pea albumin protein.

2. The method of claim 1, wherein the pea biomass comprises pea seeds.

3. The method of claim 1, wherein the extracting comprises using gravity settling or centrifugation to separate solids from the protein suspension.

4. The method of claim 1, further comprising adding a flocculant to the pea biomass.

5. The method of claim 4, wherein the flocculant comprises alkylamine epichlorohydrin, polydimethyldiallylammonium chloride, or a polyamine.

6. The method of claim 4, wherein the flocculant comprises alkylamine epichlorohydrin.

7. The method of claim 1, wherein the PEG has a molecular weight of about 3000 to about 10,000.

8. The method of claim 1, wherein the PEG has a molecular weight of about 8000.

9. The method of claim 1, wherein the PEG is present at a volume concentration of 2% to 50%.

10. The method of claim 1, wherein the salt comprises sodium chloride, magnesium sulfate, or a mixture thereof.

11. The method of claim 1, wherein the salt is added to the protein suspension to attain a concentration of about 100 mM to about 2M.

12. The method of claim 1, wherein the step of subjecting the dialyzed or ultrafiltered protein solution to one or more concentrating or filtering steps comprises diafiltering the dialyzed or ultrafiltered protein solution.

13. The method of claim 1, wherein the step of subjecting the dialyzed or ultrafiltered protein solution to one or more concentrating or filtering steps comprises concentrating and filtering the dialyzed or ultrafiltered protein solution to generate a pea albumin protein concentrate.

14. The method of claim 13, further comprising sterilizing the pea albumin protein concentrate to obtain a sterilized pea albumin protein concentrate, and drying the sterilized pea albumin protein concentrate.

15. The method of claim 1, comprising subjecting the protein suspension to ultrafiltration using a permeable membrane, wherein the membrane comprises polyethersulfone, polypropylene, polyvinylidene fluoride, polyacrylonitrile, cellulose acetate, or polysulfone.

* * * * *